(12) United States Patent
Bok et al.

(10) Patent No.: US 6,465,019 B1
(45) Date of Patent: Oct. 15, 2002

(54) HEALTH-IMPROVING SPICE COMPOSITION

(75) Inventors: Song-Hae Bok; Tae-Sook Jeong; Ki-Hwan Bae, all of Daejeon; Yong-Bok Park; Myung-Sook Choi, both of Daegu; Yong-Kook Kwon, Daejeon; Byung-Hwa Hyun, Daejeon; Yang-Kyu Choi, Daejeon; Chul-Ho Lee, Daejeon; Surk-Sik Moon, Gongju-shi, all of (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 09/680,356

(22) Filed: Oct. 5, 2000

Related U.S. Application Data

(63) Continuation of application No. PCT/KR99/00166, filed on Apr. 7, 1999.

(30) Foreign Application Priority Data

Apr. 8, 1998 (KR) .............................. 98-12410

(51) Int. Cl.$^7$ .................. A01N 65/00; A23L 1/212; A23L 1/223
(52) U.S. Cl. .................. 424/736; 426/616; 426/638
(58) Field of Search .................. 424/736; 426/616, 426/638

(56) References Cited

U.S. PATENT DOCUMENTS 6,013,304 A * 1/2000 Todd .......................... 426/638

* cited by examiner

*Primary Examiner*—Herbert J. Lilling
(74) *Attorney, Agent, or Firm*—Katten Muchin Zavis Rosenman

(57) ABSTRACT

The present invention relates to a spice composition comprising 1 to 30 % by weight of garlic, 10 to 50% by weight of onion, 0.2 to 10% by weight of ginger, 5 to 40% by weight of jujube, and 10 to 50% by weight of citrus peel or an extract thereof or 1 to 20% by weight of naringin or hesperidin.

16 Claims, No Drawings

HEALTH-IMPROVING SPICE COMPOSITION

This application is a continuation of international application Ser. No. PCT/KR99/00166, filed on Apr. 7, 1999, which is pending.

FIELD OF THE INVENTION

The present invention relates to a health-improving spice composition and, more particularly, it pertains to a spice composition comprising 1 to 30% by weight of garlic, 10 to 50% by weight of onion, 0.2 to 10% by weight of ginger, 5 to 40% by weight of jujube, and 10 to 50% by weight of citrus peel or an extract thereof or 1 to 20% by weight of naringin or hesperidin.

BACKGROUND OF THE INVENTION

In recent years, an increasing number of the adult population have been afflicted with such diseases as cancer and cardio-circulatory disorders and it has been reported that such diseases can be prevented by improving the diet.

Onion, garlic and ginger are common raw materials for preparing spices in Korea. Garlic is known to have an anti-cancer activity together with activities for preventing cardio-circulatory diseases, promoting circulation of the blood and strengthening the immune system(L.D. Lawson, "Bioactive Organosulfur Compounds of Garlic and Garlic Products: Role in Reducing Blood Lipids", in *Human Medicinal Agents*, 306–330, D. Kinghorn and M. F. Balaandrin Eds., ACS symposium Series, 534, 1993). Onion has been reported to be useful in preventing cardio-circulatory diseases; it lowers the blood cholesterol level, increases the blood high-density lipoprotein(HDL) level and inhibits the platelet aggregation(J. Carper, *Food Pharmacy*, Batam Books (1989)).

Hitherto, citrus peels have been discarded or used only for the preparation of an animal fodder or organic fertilizer. Dried citrus peel comprises 50 to 60 wt % of alcohol-insoluble polymers such as pectin, hemicellulose and cellulose; 30 to 50 wt % of alcohol-soluble solid materials(80 wt % thereof consisting of glucose, fructose and sucrose); and a small or trace amount of bioflavonoids, vitamins, limonoids, phenolic compounds and oils. In particular, various bioflavonoids listed in Table I are present in the citrus peel (Horowitz, R. M., et al., *J. Org. Chem.*, 25, 2183–2187 (1960)). Among the bioflavonoids, hesperidin is a major component of oranges, lemons and tangerines; naringin is a major component of grapefruits; and nearly the same amounts of naringin and hesperidin are present in citron.

TABLE I

| Citrus fruit | Bioflavonoids |
| --- | --- |
| Grapefruit | apigenin, dihydrokaempferol, eriodictyol, hesperetin, hesperidin, isorhamnetin, isosakuranetin, kaempferol, naringenin, naringin, neohesperidin, poncirin, quercetin, rutin |
| Lemon | apigenin, apigenin 7-rutinoside, chrysoeriol, diosmin, eriocitrin, hesperidin, isorhamnetin, limocitrin, limocitrol, luteolin 7-rutinoside, naringin, neohesperidin, poncirin, quercetin |

TABLE I-continued

| Citrus fruit | Bioflavonoids |
| --- | --- |
| Orange | auranetin, hesperidin, isosakuranetin 7-rutinoside, naringin, neohesperidin, nobiletin, rutin, sinensetin, tangeretin, vitexin |
| Tangerine | hesperidin, nobiletin, tangeretin |

It has been reported that the bioflavonoids isolated from a citrus peel have anti-oxidative, anti-cancer, anti-viral and blood-pressure lowering activities (Saija, A., et al., *Free Radical Biol. Med.*, 19, 481–486(1995); Matsubara, Y., et al., *Japan Organic Synthesis Chem. Association Journal*, 52, 318–327(1994, Mar.); Galati, E. M., et al., *Farmaco.*, 51(3), 219–221(1996, Mar.); Felicia, V., et al., Nutr. Cancer, 26, 167–181(1996); EP 0352147A2(1990. 1. 24); and Kaul, T. N., et al.,*J. Med. Viol.*, 15, 71–75(1985)). Further, limonoids present in the citrus peel have been reported to have an anti-cancer activity(Lam, L. K. T., et al., Inhibition of Chemically Induced Carcinogenesis by Citrus Limonoids, In *Food Phytochemicals for Cancer Prevention*, Vol. I, ACS Symposium series No. 546, M. T. Huang, O. Osawa, C. T. Ho, R. Rosen(eds), 1993).

However, hitherto, no spice compositions containing citrus peel or an extract thereof have been reported. The present inventors have endeavored to develop a health-improving spice composition and have discovered that a spice composition comprising onion, garlic, ginger, jujube and citrus peel or an extract thereof is very helpful for preventing adult diseases such as cancer, hypertension and cardio-circulatory diseases.

SUMMARY OF THE INVENTION

Accordingly, it is an object of the present invention to provide a novel health-improving spice composition.

DETAILED DESCRIPTION OF THE INVENTION

In accordance with one aspect of the present invention, there is provided a spice composition comprising 1 to 30% by weight of garlic, 10 to 50% by weight of onion, 0.2 to 10% by weight of ginger, 5 to 40% by weight of jujube, and 10 to 50% by weight of citrus peel or an extract thereof. The spice composition may further comprises 20 to 50% by weight of oatmeal powder, the resulting spice composition being preferably employed in the production of a hamburger sauce or a steak sauce.

Preferably, the inventive spice composition may comprise 5 to 25% by weight of garlic, 15 to 40% by weight of onion, 0.5 to 5% by weight of ginger, 10 to 35% by weight of jujube and 15 to 40% by weight of citrus peel or an extract thereof. 20 to 50% by weight of oatmeal powder may also be added thereto.

On the other hand, the spice composition may comprise 1 to 20% by weight, preferably, 5 to 15% by weight of naringin or hesperidin instead of the citrus peel or an extract thereof.

Further, the spice composition may further comprise additional ingredients such as pepper, red pepper, green onion, spring onion and sesame, if necessary.

The citrus may be tangerine, orange, lemon, grapefruit, citron, *Poncirus trifoliata* and the like. It is preferable to use the peel of citrus fruits produced by organic agricultural techniques without using chemical pesticides.

The citrus peel extract of the present invention may be prepared by any of the conventional methods using water or a suitable solvent such as aqueous alcohols, Ca(OH)$_2$ and NaOH. For instance, 3 to 30 l of 20 to 95% ethanol is added to 1 kg of dried citrus peel and the mixture is allowed to stand at a temperature ranging from 25 to 80° C. for a period ranging from 1 to 12 hours. The resulting extract is filtered and the filtrate is concentrated, e.g., by vacuum, to obtain a concentrated peel extract. Alternatively, 5 to 30 l of 0.1 to 2% Ca(OH)$_2$ or NaOH is added to 1 kg of dried citrus peel and the mixture is allowed to stand at a temperature ranging from 25 to 60° C. for a period ranging from 1 to 5 hours. The resulting extract is filtered and the filtrate is adjusted to a pH ranging from 4.0 to 7.0 by adding 1 N HCl thereto. The resulting filtrate is allowed to stand at a temperature ranging from 1 to 10° C. for a period ranging from 10 to 48 hours. The resulting precipitate is recovered and then dried to obtain a citrus peel extract.

The spice composition of the present invention is healthful since the citrus peel or an extract thereof exerts inhibitory effects on the 3-hydroxy-3-methylglutaryl CoA(HMG-CoA) reductase activity and acyl CoA-cholesterol-o-acyltransferase (ACAT) activity, thereby preventing various cardio-circulatory diseases caused by high plasma cholesterol level. Further, the citrus peel or an extract thereof also exhibits various health-improving activities such as an anti-cancer, anti-viral and blood pressure-lowering activities. Moreover, onion, garlic, ginger and jujube contained therein also have preventive activities against cardio-circulatory diseases.

In spite of its potent efficacies, the inventive spice composition shows little toxicity or mitogenicity in animal tests. More specifically, the spice composition exhibits no toxicity when it is orally administered to mice at a dose of 1,000 mg/kg, which corresponds to an oral administration dose of 50 to 100 g/kg body weight of citrus peel extract for a person weighing 50 kg. Further, the citrus peel extract exerts no adverse effects on the liver function.

The spice composition of the present invention may be prepared by mixing garlic, onion, ginger, jujube and citrus peel or an extract thereof, adding water to the resulting mixture, and blending the mixture. A powdered spice composition may be prepared by drying and pulverizing the blended spice composition. In the preparation of the inventive spice composition, garlic, onion and ginger are employed after peeling and washing with water, and jujube, after washing with water and removing the seed therefrom. The inventive spice composition has a good flavor and taste primarily due to the addition of jujube.

For the health-improving or disease-preventive purposes, the spice composition of the present invention may be used in an amount ranging from 10 to 100 g per 1 kg of food. For instance, the spice composition may be added to hamburger steaks during roast, or fish, meat or poultry, e.g., chicken, duck and turkey, may be cooked with the inventive spice composition to prepare health-improving food. Further, the spice composition may be added to cooked food and may also be used like a conventional spice.

The following Examples are intended to further illustrate the present invention without limiting its scope.

Further, percentages given below for solid in solid mixture, liquid in liquid, and solid in liquid are on a wt/wt, vol/vol and wt/vol basis, respectively, and all the reactions were carried out at room temperature, unless specifically indicated otherwise.

EXAMPLE 1

Preparation of Citrus Peel Extract (1) Method using Ethanol

The peel of tangerine (Cheju island, Korea) was dried at room temperature and 5 l of 30% ethanol was added to 500 g of the dried peel. The peel was extracted at 60° C. for 5 hours. The extract thus obtained was filtered through cotton cloths and the filtrate was concentrated under a vacuum to obtain 190 g of a syrupy extract.

To analyze the composition of the citrus peel extract obtained above, 5.0 $\mu$l. of the resulting extract was subjected to high performance liquid chromatography (HPLC) using Lichrosorb RP-8 column(5 $\mu$m, 4×250 mm) which was pre-equilibrated with 37% methanol and maintained at 30° C. The extract was eluted with 37% methanol at a flow rate of 1.0 ml/min. Standard solutions were prepared by dissolving hesperidin and naringin(Sigma Chemical Co. U.S.A.) in methanol to final concentrations of 0.1, 0.2, 0.3, 0.4 and 0.5 mg/ml, respectively, and subjected to HPLC under the same condition as above. The eluates were detected at 280 nm with UV-VIS spectrophotometer and the contents of hesperidin and naringin were calculated by comparing the HPLC scans of the citrus peel extract and the standard solutions. It was found that the citrus peel extract contained 5.1 g of hesperidin.

Further, the composition of the citrus peel extract was analyzed to contain 65% of moisture, 28% of sugar(11% fructose, 11% glucose and 6% sucrose), 2.7% of hesperidin and other trace ingredients such as ashes.

(2) Method Using Ca(OH)$_2$

The peel of tangerine (Cheju island, Korea) was dried at room temperature and 5 l of 0.5% Ca(OH)$_2$ solution was added to 500 g of the dried peel. The peel was extracted at room temperature for 1 hour while stirring and the extract thus obtained was filtered through cotton cloths. 1N HCl was added to the filtrate to adjust its pH to 4.5. This procedure was repeated to obtain a second filtrate which was adjusted to pH 6.8. The two filtrates thus obtained were allowed to stand at 5° C. for 24 hours to form precipitates. The precipitates thus obtained were recovered and dried to obtain 5 g and 10 g of powders, respectively. HPLC analysis of the powers demonstrated that the citrus peel extracts contained 3.2 g and 6.55 g of hesperidin(purity: 64% and 65%), respectively.

(3) Method Using NaOH

The peel of tangerine(Cheju island, Korea) was dried at room temperature and 5 l of 0.5% NaOH was added to 500 g of the dried peel. The peel was extracted at room temperature for 1 hour while stirring and the extract thus obtained was filtered through cotton cloths. 1 N HCl was added to the filtrate to adjust its pH to 4.5. This procedure was repeated to obtain a second filtrate which was adjusted to pH 6.8. The two filtrates thus obtained were allowed to stand at 5° C. for 24 hours to form precipitates. The precipitates thus obtained were recovered and dried to obtain 44 g and 49 g of powders, respectively. HPLC analysis of the powers demonstrated that the citrus peel extracts contained 13.6 g and 9.8 g of hesperidin(purity: 31% and 20%), respectively.

EXAMPLE 2

Preparation of Spice Composition

Onions, garlics and gingers produced in Korea were peeled and washed with water. Jujube was washed with water and the seed was removed. The peel of citrus fruits produced by organic agricultural techniques without using chemical pesticides were washed with water. These materials were then air-dried in the shade or oven-dried. Dried jujube and citrus peel were powdered with a pulverizer.

200 g of dried onion, 50 g of dried garlic, 10 g of dried ginger, 80 g of jujube powder and 200 g of citrus peel powder were mixed together, 1,000 ml of water was added thereto and the mixture was homogenized with a blender.

For a long-term storage, the spice composition thus prepared was sterilized at 121° C. or was dried and powdered.

EXAMPLE 3

Preparation of Steak Sauce

Dried onion, garlic and ginger, jujube powder and citrus peel powder were prepared as in Example 2. 200 g of dried onion, 50 g of dried garlic, 10 g of dried ginger, 80 g of jujube powder, 200 g of citrus peel powder and 260 g of oatmeal powder were mixed together, 1,000 ml of water was added thereto, and the mixture was homogenized with a blender.

For a long-term storage, the spice composition thus prepared was sterilized at 121° C. or was dried and powdered.

EXAMPLES 4 to 8

Preparation of Spice Compositions

Various spice compositions were prepared in accordance with the procedure of Example 2 or 3 by employing the ingredients listed in Table II.

TABLE II

| | Contents (g) | | | | |
|---|---|---|---|---|---|
| Ingredients | Ex. 4 | Ex. 5 | Ex. 6 | Ex. 7 | Ex. 8 |
| Citrus peel powder | — | 120 | 130 | — | — |
| Citrus peel extract*[1] | 150 | — | — | — | — |
| Naringin | — | — | — | 65 | — |
| Hesperidin | — | — | — | — | 100 |
| Dried jujube | 80 | 100 | 135 | 190 | 140 |
| Dried onion | 150 | 120 | 115 | 250 | 200 |
| Dried ginger | 10 | 10 | 15 | 15 | 10 |
| Dried garlic | 50 | 40 | 130 | 130 | 100 |
| Oatmeal powder | — | — | 350 | — | — |

*[1]Prepared in Example 1 (1)

EXAMPLE 9

Beneficial Effects of Ingesting the Inventive Spice Composition: an Animal Test 20 four-week-old Sprague-Dawley rats (Taihan laboratory animal center, Korea) each weighing about 90 to 110 g were evenly divided into two dietary groups by a randomized block design. The rats of the two groups were fed with two different high-cholesterol diets, i.e., AIN-76 laboratory animal diet (ICN Biochemicals, Cleveland, Ohio, U.S.A.) containing 1% cholesterol(Control group), and 1% cholesterol plus 12.2% spice composition(4.5% citrus peel powder, 2% jujube powder, 4.5% onion powder, 0.2% ginger powder and 1% garlic powder), respectively. The compositions of diets fed to the two groups are shown in Table III.

TABLE III

| | Dietary group | |
|---|---|---|
| Ingredients | Control group | Spice composition group |
| Casein | 20 | 19 |
| D,L-methionine | 0.3 | 0.3 |
| Corn starch | 15 | 14.5 |
| Sucrose | 49 | 39.0 |
| Cellulose powder*[1] | 5 | 4.8 |
| Mineral mixture*[1] | 3.5 | 3.0 |
| Vitamin mixture*[1] | 1 | 1 |
| Choline bitartrate | 0.2 | 0.2 |
| Corn oil | 5 | 5 |
| Cholesterol | 1 | 1 |
| Citrus peel powder | — | 4.5 |
| jujube powder | — | 2.0 |
| onion powder | — | 4.5 |
| ginger powder | — | 0.2 |
| garlic powder | — | 1.0 |
| Total | 100 | 100 |

*[1]Purchased from TEKLAD premier Co. (Madison, WI, U.S.A.)

The rats were allowed to feed freely on the specified diet together with water for eight weeks, the ingestion amount was recorded daily and the rats were weighed every 7 days, and then the record was analyzed. All rats showed a normal growth rate and there was observed no significant difference among the two groups in terms of the feed ingestion amount and the weight gain.

Thereafter, the effect of administering the spice composition to rats on the plasma cholesterol and neutral lipid content was determined as follows.

Each of the blood samples taken from the rats of the two dietary groups was allowed to stand at room temperature for 2 hours, and centrifuged at 3,000 rpm for 15 minutes to obtain a supernatant (serum), which was stored in a freezer until the analysis.

Total cholesterol (TC) level of each blood sample was directly determined with a blood chemistry analyzer (CIBA Corning 550 Express, U.S.A.). In order to determine HDL-cholesterol level, an HDL-determining reagent (Chiron Diagnostics Co., U.S.A.), which was prepared by applying the HDL quantification method employing dextran sulfate and magnesium sulfate (Warnick, G. R. et al., *Clin. Chem.*, 28, 1379–1388(1982)), was mixed with each serum sample in a ratio of 1:10(v/v) and the mixture was reacted at 20 to 25° C. for 5 minutes in an incubator. The resultant was centrifuged at 2,500 rpm for 10 minutes to obtain a supernatant, which was then analyzed with a blood chemistry analyzer.

Significance test(student t-test) of the analyzed values from each mice was carried out by employing a computer software (Microsoft Excel, Ver. 7.0). The result is shown in Table IV.

TABLE IV

| | Group | |
|---|---|---|
| Lipid Conc. | Control group | Spice composition group |
| Total-Cholesterol (mg/dl) | 151 ± 7.2 | 137.2 ± 8.7 |
| HDL-Cholesterol (mg/dl) | 47.7 ± 3.0 | 71.3 ± 5.8 |

TABLE IV-continued

| Lipid Conc. | Group | |
|---|---|---|
| | Control group | Spice composition group |
| HDL-Cholesterol Total-Cholesterol (%) | 31.5 ± 2.4 | 52.0 ± 2.9 |

As shown in Table IV, the total cholesterol level of the rats fed with the inventive spice composition decreased by 10%, as compared with that of the control group. In particular, the plasma HDL level increased by about 50% in the spice composition group, as compared with that of the control group. This result demonstrates that ingestion of the inventive spice composition increases plasma HDL level while decreasing plasma cholesterol level, thereby contributing to the prevention of cardio-circulatory diseases.

EXAMPLE 10

Toxicity of Orally Administered Spice Composition 7 to 8 week-old, specific pathogen-free ICR female mice(6 heads) each weighing about 25 to 29 g and male mice(6 heads) each weighing about 34 to 38 g were bred under a condition of 22±1° C., 55±5% moisture and 12L/12D photoperiod. Fodder (mouse and rat fodder, Cheiljedang Co., Korea) and water were sterilized and fed to the mice.

The spice composition prepared in Example 2 was dissolved in 0.5% Tween® 80 to a concentration of 100 mg/ml, and the solution was orally administered to the mice in an amount of 0.2 ml per 20 g of mouse body weight. The solution was administered once and the mice were observed for 10 days for signs of adverse effects or death according to the following schedule: 1, 4, 8, and 12 hours after the administration and, every 12 hours thereafter. The weight changes of the mice were recorded every day to examine the effect of the spice composition. Further, on the 10th day, the mice were sacrificed and the internal organs were visually examined.

All the mice were alive at day 10 and the spice composition showed no toxicity at a dose of 1,000 mg/kg. The autopsy revealed that the mice had not developed any pathological abnormality, and no weight loss was observed during the 10 day test period. Accordingly, it was concluded that the spice composition is not toxic when orally administered to an animal.

EXAMPLE 11

Effect of Ingesting Citrus Peel Extract in ACAT Inhibition (Step 1) Feeding of Citrus Peel Extract to Test Animals 20 four-week-old Sprague-Dawley rats (Taihan laboratory animal center, Korea) each weighing about 90 to 110 g were evenly divided into two dietary groups by a randomized block design. The rats of the two groups were fed with two different high-cholesterol diets, i.e., AIN-76 laboratory animal diet(ICN Biochemicals, Cleveland, Ohio, U.S.A.) containing 1% cholesterol(Control group), and 1% cholesterol plus 16.7% citrus peel extract obtained in Example 1(1), respectively. The compositions of diets fed to the two groups are shown in Table V.

TABLE V

| Ingredients | Dietary group | |
|---|---|---|
| | Control group | Citrus peel extract[*2] group |
| Casein | 20 | 20 |
| D,L-methionine | 0.3 | 0.3 |
| Corn starch | 15 | 15 |
| Sucrose | 49 | 32.3 |
| Cellulose powder[*1] | 5 | 5 |
| Mineral mixture[*1] | 3.5 | 3.5 |
| Vitamin mixture[*1] | 1 | 1 |
| Choline bitartrate | 0.2 | 0.2 |
| Corn Oil | 5 | 5 |
| Cholesterol | 1 | 1 |
| Citrus peel extract | — | 16.7 |
| Total | 100 | 100 |

[*1]Purchased from TEKLAD premier Co. (Madison, WI, U.S.A.)
[*2]0.1% hesperidin equivalent The rats were allowed to feed freely on the specified diet together with water for six weeks, the ingestion amount was recorded daily and the rats were weighed every 7 days, and then the record was analyzed. All rats showed a normal growth rate and there was observed no significant difference among the two groups in terms of the feed ingestion amount and the weight gain.

(Step 2) Preparation of Microsomes

To determine the effect of feeding the citrus peel extract to rats on the activity of ACAT, microsomes were separated from the liver tissue to be used as an enzyme source.

First, the rats of the two groups were sacrificed by decapitation and the livers were excised. 1 g each of the livers was homogenized in 5 ml of homogenization medium (0.1 M $KH_2PO_4$, pH 7.4, 0.1 mM EDTA and 10 mM β-mercaptoethanol). The homogenate was centrifuged at 3,000×g for 10 min. at 40° C. and the supernatant thus obtained was centrifuged at 15,000×g for 15 min. at 40° C. to obtain a supernatant. The supernatant was put into an ultracentrifuge tube (Beckman) and centrifuged at 100,000×g for 1 hour at 40° C. to obtain microsomal pellets, which were then suspended in 3 ml of the homogenization medium and centrifuged at 100,000×g for 1 hour at 40° C. The pellets thus obtained were suspended in 1 ml of the homogenization medium. The concentration of proteins in the resulting suspension was determined by Lowry's method and then adjusted to 4 to 8 mg/ml. The resulting suspension was stored in a deep freezer (Biofreezer, Forma Scientific Inc.).

(Step 3) ACAT Assay 6.67 μl of 1 mg/ml cholesterol solution in acetone was mixed with 6 μl of 10% Triton WR-1339 (Sigma Co.) in acetone and, then, acetone was removed from the mixture by evaporation under a nitrogen flow. Distilled water was added to the resulting mixture to a cholesterol concentration of 30 mg/ml.

To 10 μl of the resulting aqueous cholesterol solution were added 10 μl of 1 M $KH_2PO_4$(pH 7.4), 5 μl of 0.6 mM bovine serum albumin (BSA), 10 μl of microsome solution obtained in (Step 2) and 55 μl of distilled water(total 90 μl). The mixture was pre-incubated in a 37° C. waterbath for 30 min.

10 μl of ($1-^{14}C$) oleoyl-CoA solution(0.05 μCi, final concentration: 10 μM) was added to the pre-incubated mixture and the resulting mixture was incubated in a 37° C. waterbath for 30 min. Added to the mixture were 500 μl of isopropanol:heptane mixture (4:1 (v/v)), 300 μl of heptane and 200 μl of 0.1 M $KH_2PO_4$(pH 7.4), and the mixture was mixed thoroughly with a vortex mixer and then allowed to stand at room temperature for 2 min.

200 μl of the resulting supernatant was put in a scintillation bottle and 4 ml of scintillation fluid (Lumac) was added thereto. The mixture was assayed for radioactivity with 1450 Microbeta liquid scintillation counter (Wallacoy, Finland). ACAT activity was calculated as picomoles of cholesteryl oleate synthesized per min. per mg protein (pmoles/min/mg protein). The result is shown in

TABLE VI

| Group | ACAT activity (pmole/min/mg protein) | % Inhibition on ACAT activity |
|---|---|---|
| Control group | 806.2 ± 105.2 | 0 |
| Citrus peel extract group | 548.0 ± 65.4 | 32 |

As can be seen in Table VI, ACAT activity observed for the rats in the citrus peel extract group is lower than that of the control group by 32%.

EXAMPLE 12

Effect of Ingesting Citrus Peel Extract in HMG-CoA Reductase Inhibition (Step 1) Preparation of Microsomes To determine the effect of feeding citrus peel extract to rats on the activity of HMG-CoA reductase, a regulatory enzyme of the cholesterol synthesis in the liver, microsomes were separated from the liver tissue to be used as an enzyme source.

First, the rats of the two groups prepared as in (Step 1) of Example 11 were sacrificed by decapitation and the livers were excised and immediately placed in an ice-cold homogenization medium(50 mM $KH_2PO_4$(pH 7.0), 0.2M sucrose, 2 mM dithiothreitol (DTT)). The livers were homogenized in the homogenization medium(2 ml medium/g of the liver) with a Waring blender for 15 sec. (three strokes with a motor-driven Teflon pestle in a Potter-Elvehjem type glass homogenizer). The homogenate was centrifuged at 15,000×g for 10 min. and the supernatant thus obtained was centrifuged at 100,000×g for 75 min. to obtain microsomal pellets, which were then resuspended in the homogenization medium containing 50 mM EDTA and centrifuged at 100,000×g for 60 min. The supernatant containing the microsome was used as an enzyme source.

(Step 2) HMG-CoA Reductase Assay

The activity of HMG-CoA reductase was determined by employing [$^{14}$C]HMG-COA, in accordance with the method of Shapiro et al. (*Biochemica et Biophysica Acta*, 370, 369–377(1974)) as follows.

The enzyme in the supernatant containing the microsome obtained in (Step 1) was activated at 37° C. for 30 min. Added to a reaction tube were 20 μl of HMG-CoA reductase assay buffer(0.25 M $KH_2PO_4$(pH 7.0), 8.75 mM EDTA, 25 mM DTT, 0.45 M KCl and 0.25 mg/ml BSA), 5 μl of 50 mM NADPH, 5 μl of [$^{14}$C]HMG-CoA(0.05 μCi/tube, final conc. 120 μM), and 10 μl of activated microsomal enzyme (0.03–0.04 mg), and the mixture was incubated at 37° C. for 30 min. The reaction was terminated by adding 10 μl of 6 M HCl to the mixture, and the mixture was incubated at 37° C. for 15 min. to allow complete lactonization of the product (mevalonate). The precipitate was removed by centrifugation at 10,000×g for 1 min. and the supernatant was applied to a Silica gel 60G TLC plate (Altech, Inc., Newark, U.S.A.) and then developed with benzene:acetone(1:1, v/v). A region having a Rf value ranging from 0.65 to 0.75 was removed by scraping with a disposable cover slips and assayed for radioactivity with 1450 Microbeta liquid scintillation counter(Wallacoy, Finland). Enzyme activities were calculated as picomoles mevalonic acid synthesized per min. per mg protein (pmoles/min/mg protein). The result is shown in

TABLE VII

| | Group | |
|---|---|---|
| | Control group | Citrus peel extract group |
| HMG-CoA reductase activity (pmole/min/mg protein) | 147 +12.5 | 112.1 +12.8 |

As can be seen from the result in Table VII, rats in the control group rats showed a relatively high HMG-COA reductase activity, while the HMG-COA activity observed with rats in the citrus peel extract group is lower than that of the control group by 34%.

While the invention has been described with respect to the above specific embodiments, it should be recognized that various modifications and changes may be made to the invention by those skilled in the art which also fall within the scope of the invention as defined by the appended claims.

What is claimed is:

1. A spice composition comprising 1 to 30% by weight of garlic, 10 to 50% by weight of onion, 0.2 to 10% by weight of ginger, 5 to 40% by weight of jujube, and 10 to 50% by weight of citrus peel or an extract thereof, wherein the citrus peel extract is prepared by a process having the steps of adding ethanol to dried citrus peel, allowing the mixture to stand at a temperature ranging form 25 to 80° C., filtering the resulting extract and concentrating the filtrate to obtain the citrus peel extract.

2. The spice composition of claim 1 which comprises 5 to 25% by weight of garlic, 15 to 40% by weight of onion, 0.5 to 5% by weight of ginger, 10 to 35% by weight of jujube and 15 to 40% by weight of citrus peel or an extract thereof.

3. The spice composition of claim 1 which further comprises 20 to 50% by weight of oatmeal powder.

4. The spice composition of claim 3 which comprises 5 to 25% by weight of garlic, 15 to 40% by weight of onion, 0.5 to 5% by weight of ginger, 10 to 35% by weight of jujube, 15 to 40% by weight of citrus peel or an extract thereof, and 20 to 50% by weight of oatmeal powder.

5. The spice composition of claim 1, wherein the citrus is tangerine, orange, lemon, grapefruit, citron or *Poncirus trifoliata*.

6. The spice composition of claim 1, wherein the citrus peel extract is prepared by a process having the steps of: adding 3 to 30 l of 20 to 95% ethanol to 1 kg of dried citrus peel; allowing the mixture to stand at a temperature ranging from 25 to 80° C. for a period ranging from 1 to 12 hours; filtering the resulting extract; and concentrating the filtrate to obtain the citrus peel extract.

7. A process for preparing a spice composition comprising the steps of mixing 1 to 30% by weight of garlic, 10 to 50% by weight of onion, 0.2 to 10% by weight of ginger, 5 to 40% by weight of jujube, and 10 to 50% by weight of citrus peel or an extract thereof, adding water to the resulting mixture, and blending the mixture, wherein the citrus peel extract is prepared by a process having the steps of adding ethanol to dried citrus peel, allowing the mixture to stand at a temperature ranging from 25 to 80° C., filtering the resulting extract and concentrating the filtrate to obtain the citrus peel extract.

8. The process of claim 7, further comprising a step of adding oatmeal powder to the spice composition.

9. A spice composition comprising 1 to 30% by weight of garlic, 10 to 50% by weight of onion, 0.2 to 10% by weight of ginger, 5 to 40% by weight of jujube, and 10 to 50% by weight of citrus peel or an extract thereof, wherein the citrus peel extract is prepared by a process having the steps of adding aqueous $Ca(OH)_2$ or aqueous NaOH to dried citrus peel; allowing the mixture to stand at a temperature ranging from 25 to 60° C., filtering the resulting extract; adjusting the filtrate to a pH ranging from 4.0 to 7.0; allowing the resulting filtrate to stand at a temperature ranging form 2 to 10° C.; and, recovering and drying the resulting precipitate to obtain the citrus peel extract.

10. The spice composition of claim 9 which comprises 5 to 25% by weight of garlic, 15 to 40% by weight of onion, 0.5 to 5% by weight of ginger, 10 to 35% by weight of jujube and 15 to 40% by weight of citrus peel or an extract thereof.

11. The spice composition of claim 9 which further comprises 20 to 50% by weight of oatmeal powder.

12. The spice composition of claim 11 which comprises 5 to 25% by weight of garlic, 15 to 40% by weight of onion, 0.5 to 5% by weight of ginger, 10 to 35% by weight of jujube, 15 to 40% by weight of citrus peel or an extract thereof, and 20 to 50% by weight of oatmeal powder.

13. The spice composition of claim 9 wherein the citrus is tangerine, orange, lemon, grapefruit, citron or *Poncirus trifoliata*.

14. The spice composition of claim 9, wherein the citrus peel extract is prepared by a process having the steps of: adding 5 to 30 l of 0.1 to 2% $Ca(OH)_2$ or NaOH solution to 1 kg of dried citrus peel; allowing the mixture to stand at a temperature ranging form 25 to 60° C. for a period ranging from 1 to 5 hours; filtering the resulting extract; adjusting the filtrate to a pH ranging from 4.0 to 7.0; allowing the resulting filtrate to stand at a temperature ranging from 1 to 10° C. for a period ranging from 10 to 48 hours; and recovering and drying the resulting precipitate to obtain the citrus peel extract.

15. A process for preparing a spice composition comprising the steps of mixing 1 to 30% by weight of garlic, 10 to 50% by weight of onion, 0.2 to 10% by weight of ginger, 5 to 40% by weight of jujube, and 10 to 50% by weight of citrus peel or an extract thereof, adding water to the resulting mixture, and blending the mixture, wherein the citrus peel extract is prepared by a process having the steps of adding aqueous $Ca(OH)_2$ or aqueous NaOH to dried citrus peel; allowing the mixture to stand at a temperature ranging from 25 to 60° C., filtering the resulting extract; adjusting the filtrate to a pH ranging from 4.0 to 7.0; allowing the resulting filtrate to stand at a temperature ranging from 1 to 10° C.; and recovering and drying the resulting precipitate to obtain the citrus peel extract.

16. The process of claim 15, further comprising a step of adding oatmeal to the spice composition.

\* \* \* \* \*